United States Patent [19]
Zeldis et al.

[11] Patent Number: 5,985,914
[45] Date of Patent: Nov. 16, 1999

[54] TREATMENT OF INFLAMMATORY DISORDERS OF THE BOWEL AND URINARY BLADDER

[75] Inventors: Jerome Zeldis, Princeton, N.J.; Susan McLaughlin, Phoenixville; Bruce Stouch, Newtown Square, both of Pa.

[73] Assignee: Therakos, Inc., Exton, Pa.

[21] Appl. No.: 09/111,829

[22] Filed: Jul. 8, 1998

Related U.S. Application Data

[60] Provisional application No. 60/052,101, Jul. 10, 1997.

[51] Int. Cl.⁶ .......................... A61K 31/35; A61K 31/34; A61M 37/00
[52] U.S. Cl. .......................... 514/455; 514/451; 514/454; 514/461; 514/468; 604/4
[58] Field of Search .................... 514/455, 451, 514/454, 461, 468; 604/4

[56] References Cited

U.S. PATENT DOCUMENTS

| | | | |
|---|---|---|---|
| D. 298,279 | 10/1988 | Lee et al. | D24/51 |
| D. 298,567 | 11/1988 | Morris | D24/1.1 |
| D. 299,531 | 1/1989 | Troutner et al. | . |
| D. 299,953 | 2/1989 | King et al. | D24/1.1 |
| 4,196,281 | 4/1980 | Hearst et al. | 536/28 |
| 4,321,919 | 3/1982 | Edelson | 128/214 R |
| 4,398,906 | 8/1983 | Edelson | 604/6 |
| 4,428,744 | 1/1984 | Edelson | 604/6 |
| 4,452,811 | 6/1984 | della Ville | 424/281 |
| 4,464,166 | 8/1984 | Edelson | . |
| 4,464,354 | 8/1984 | Bisagni et al. | 424/59 |
| 4,465,691 | 8/1984 | Bisagni et al. | 424/256 |
| 4,568,328 | 2/1986 | King | 604/6 |
| 4,573,960 | 3/1986 | Goss | 604/6 |
| 4,573,961 | 3/1986 | King | 604/6 |
| 4,573,962 | 3/1986 | Troutner | 604/6 |
| 4,578,056 | 3/1986 | King et al. | 604/6 |
| 4,596,547 | 6/1986 | Troutner | 604/4 |
| 4,612,007 | 9/1986 | Edelson | 604/5 |
| 4,613,322 | 9/1986 | Edelson | 604/6 |
| 4,623,328 | 11/1986 | Hartranft | 604/4 |
| 4,643,710 | 2/1987 | Troutner | 494/60 |
| 4,681,568 | 7/1987 | Troutner | 604/250 |
| 4,683,889 | 8/1987 | Edelson | 128/395 |
| 4,684,521 | 8/1987 | Wdelson | 424/101 |
| 4,687,464 | 8/1987 | Troutner | 604/4 |
| 4,692,138 | 9/1987 | Troutner et al. | 604/4 |
| 4,693,981 | 9/1987 | Wiesehahn et al. | 435/238 |
| 4,705,498 | 11/1987 | Goss | 604/6 |
| 4,708,715 | 11/1987 | Troutner et al. | 604/6 |
| 4,726,949 | 2/1988 | Miripol et al. | 424/101 |
| 4,727,027 | 2/1988 | Wiesehahn et al. | 435/173 |
| 4,737,140 | 4/1988 | Lee et al. | 604/4 |
| 4,748,120 | 5/1988 | Wiesehahn et al. | 435/173 |
| 4,838,852 | 6/1989 | Edelson et al. | 604/4 |
| 4,866,282 | 9/1989 | Miripol et al. | 250/455.1 |
| 4,897,789 | 1/1990 | King et al. | 364/413.07 |
| 4,921,473 | 5/1990 | Lee et al. | 494/27 |
| 4,952,812 | 8/1990 | Miripol et al. | 250/455.1 |
| 4,960,408 | 10/1990 | Klainer et al. | 604/4 |
| 4,999,375 | 3/1991 | Bachynsky et al. | 514/455 |
| 5,030,200 | 7/1991 | Judy et al. | 604/5 |
| 5,176,921 | 1/1993 | Wiesehahn et al. | 424/529 |
| 5,216,176 | 6/1993 | Heindel et al. | 549/280 |
| 5,288,605 | 2/1994 | Lin et al. | 435/2 |
| 5,356,929 | 10/1994 | Heindel et al. | 514/455 |
| 5,360,734 | 11/1994 | Cgaonab et al. | 435/238 |
| 5,399,719 | 3/1995 | Wollowitz et al. | 549/282 |
| 5,459,030 | 10/1995 | Lin et al. | 435/2 |
| 5,482,828 | 1/1996 | Lin et al. | 435/2 |
| 5,651,993 | 7/1997 | Edelson et al. | 424/534 |

FOREIGN PATENT DOCUMENTS

| | | |
|---|---|---|
| 88302660 | 3/1988 | European Pat. Off. . |
| WO93/14791 | 1/1993 | WIPO . |
| WO95/03814 | 7/1994 | WIPO . |
| 9902215 | 1/1999 | WIPO . |

OTHER PUBLICATIONS

Richard Edelson et al. "Treatment of Cutaneous T–cell Lymphoma By Extracorporeal Photochemotherapy" New England Journal of Medicine 316:297–303 (Feb. 5, 1987).

Marglis–Nunno et al."Elimination of Potential Mutagenicity in Plantelet Concentrates that are virally Inactive with Psoralens and Ultraviolet A Light" Transformation 1985:pp. 855–862.

Hoofnagle et al. Treatment of chronic Non–A, Non–B Hepatitis with Recombinant Human Alpha interferon New England Journal of Medicine vol. 315 No. 25 pp. 1575–1578.

Davis et al. "Treatment of Chronic Hepatitis C with Recombinant Interferon Alfa" New England Journal of Medicine vol. 321 No. 22 pp. 1501–1505.

Di Bisceglie et al. "Recombinant Interferon Alfa Therapy for Chronic Hepatitis C" New England Journal of Medicine vol. 321 No. 22 pp. 1506–1510.

Farci et al "A Long–term Study of Hepitatis C Virus Replication in non–A, Non–B Hepatitis" New England Journal of Medicine vol. 325 No. 2 pp. 98–103.

Shindo et al. "Decrease in Serum Hepatitis C Viral RNA during Alpha–Interferon Therapy for Chronic Hepatitis C" Annals of Internal Medicine vol. 115 No. 9 pp. 701–704.

"High Dose Interferon Alfa–2A for the Treatment of Chronic Hepatitis C" The Annals of Pharmacotherapy 1994 Mar. vol. 28 pp. 341–342.

M. Gomez–Rubio et al. "Prolonged Treatment (18 months) of Chronic Hepatitis C with Recombinant α–Interferon in comparison with a control group" Journal of Hepatology, 1990:11:S63–S67.

(List continued on next page.)

*Primary Examiner*—Kevin E. Weddington
*Attorney, Agent, or Firm*—John W. Wallen, lll

[57] ABSTRACT

A method of treating inflammatory disorders of the bowel and inflammatory disorders of the urinary bladder are disclosed. A method of modulating the function of monocytes is also disclosed. The method involves the treatment of a patient's blood with a photoactivatable compound followed by ultraviolet light-activation of the photoactivatable compound. The blood treated as such is returned to the patient in a process known as extracorporeal photopheresis.

9 Claims, No Drawings

OTHER PUBLICATIONS

Saez–Royuela et al. "High Doses of Recombinant α–Interferon or γ–Interferon for Chronic Hepatitis C: A Randomized, Controlled Trial" Hepatology 1991; 13:No. 2 327–331.

Nakano et al. "Comparative Study of Clinical, Histological, and Immunologics Responses to Interferon Therapy in Type Non–A, Non–B, and Type B Chronic Hepatitis" The American Journal of Gastroenterology vol. 85; No. 1.1990.

Haysahi et al. "Improvement of Serum Aminotransferase Levels after Phlebotomy in Patients with chronic Active Hepatitis C and Excess Hepatic Iron" The American Journal of Gastroenterology vol. 89; No. 7.1994 pp. 986–988.

Ljunggren et al. "Plasma Levels of 8 Methoxypsoralen Determined by High–Pressure Liquid Chromatography in Psoriatic Patients Ingesting Drug from Two Manufacturers" The Journal of Investigative Dermatology, vol. 74, No. 1 pp. 59–62.

Christer T. Jansen et al. "Inter–and Intraindividual Variations in Serum Methoxsalen Levels During Repeat Oral Exposure" Therapeutic Research vol. 33, No. 2 pp. 258–264.

Micael J. Clemens et al. "Regulation of Cell Proliferation and Differentation by Interferons" Brochena J (1985) 226, 345–360.

Witter et al. "Effects of Prednisone, Aspirin, and Acetaminophen on an in vivo biologic response to interferon in humans" Clin Pharmacol Ther Aug. 1988 pp. 239–243.

Alain H. Rook et al. "Combined Therapy for Sezary Syndrome With Extracorporeal Phtochemotherapy and Low Dose Inteferon Alfa Therapy" Arch Dermatol. 1991;127: pp. 1535–1540.

Alain H. Rook, et al. "Treatment of Autoimmune Disease with Extracorporeal Photochemotherapy: Pemphigus Vulgaris" The Yale Journal of Biology and Medicine 62 (1989). 647–652.

Barr et al. "Immunomodulation with photopheresis: Clinical Results of the Multi–Center Cardiac Transplantation Study" Study supported by Therakos, A Johnson & Johnson Company.

Costanzo–Nordin et al. "Successful Treatment of Heart Transplant Rejection with Photopheresis" Transplantation vol. 53, 808–815, No. 4 Apr. 1992.

Meiser et al. Reduction of the Incidence of rejection by Adjunct Immunosuppression with Photochemotherapy After Heart Transplantation Transplantation vol. 57 563–566 No. 4 Feb. 1994.

Vowels et al. "Extracorporeal Photochemotherapy Induces the Production of Tumor Necrosis Factor–α by Monocytes: Implications for the Treatment of Cutaneous T–ell Lymphoma and Systemic Sclerosis" The Journal of Investigative Dermatology, Inc. vol. 98:686–692,1992.

Gil et al. "Hepatic and Extrahepatic HCV RNA Strands in Chronic Hepatitis C: Different Patterns of Response to Interferon Treatment Hepatology 1993; 18, 1050–1054.

Qian et al. "Replication of hepatitis C Virus in peripheral blood mononuclear cells" Journal of Hepatology 1992;16:38–383.

Eleanor C. Mandoza et al. Decreased Phorbol Myristate Acetate–Induced Release of Tumor Necrosis Factor–α and Interleukin–1β from Peripheral Blood Monocytes of Patients Chronically Infected with Hepatitis C Virus Journal of Infectious Disease 1996 vol. 174 pp. 42–44.

Zignego et al. "Infection of peripheral mononuclear blood cells by hepatitis C Virus" Journal of Hepathology, 1992;15:382–386.

"Mutsunori Shirai et al. "Introduction of Cytotoxic T Cells to a Cross–Reactive Epitope in the Hepatitis C Virus Nonstructural RNA polymerase–Like Protein" Journal of Virology, Jul. 1992;pp. 4098–4106.

Kanei et al. "Supression of hepatitis C virus RNA by interferon–λ." The Lancet vol. 336 p. 245.

Amy J. Weiner et al. "Evidence for immune selection of hepatitis C virus (HCV) putative enveolpe glycoprotein variants: Potential role in chronic HCV infections" Proc. Natl. Acad. Sci. USA vol.. 89 pp. 3468–3472.

Shimizu et al. "Early events in hepatitis C. Virus infection of chimpanzees" Proc. Natl. Acad. Sci. USA 87 pp. 6441–6444.

J. A. Garson et al. "Enhanced detection by PCR of hepatitis C virus RNA" The Lancet Oct. 6, 1990 p. 878.

P. Simmonds et al. "Classification of hepatitis C virus into six major genotypes and a series of subtypes by phylogenetic analysis of the NS–5 region" Journal of General Virology (1993). 74 2391–2399.

Houghton et al. "Monecular Biology of the Hepatitis C Virus: Implications for Diagnosis, Development and Control of Viral Disease" Hepatology vol. 14, No. 2 1991 pp. 381–388.

Choo et al. "Genetic organization and diversity of the hepatitis C virus" Proc. Natl. Acad. Sci. USA vol. 88, pp. 2451–2455.

Choo et al. "Isolation of a cDNA Clone Derived from a Blood Bond Non–A, Non–B Viral Hepatitis Genome".

Ronald L. Koretz et al. "Non–A, Non–B Posttransfusion Hepatits A Decade Later" Gastroenterology 1985:88:1251–4.

Jules L. Dienstag Non–A, Non–B Hepatitis, I. Recognition, Epidemiology, and Clinical Features Gastroenterology vol. 85, No. 2.

Flavio Rossetti, et al. "Extracorporeal Photochemotherapy as single therapy for extensive, Cutaneous, Chronic Graft–versus–Host Disease" Transplantation vol. 59 No. 1 pp. 150–151.

"American Liver Foundation" Progress, 1994–95, vol. 16 pp. 1–12.

Alain H. Rook, MD et al. "Treatment of Systemic Sclerosis With Extracorporeal Photochemotherapy" Archives of Dermatology 1992;128:337–346.

Malawista et al. "Treatment of Rheumatoid Arthritis by Extracorporeal Photochemotherapy" Arthritis and Rheumatism, vol. 34, No. 6 pp. 646–654.

Richard Edelson et al. "Treatment of Cutaneous T–Cell Lymphoma by Extracorporeal Photochemotherapy" New England Journal of Medicine 316:297–304.

Richard Edelson et al. "Photopheresis: a Clinocally Relevant Immunobiologic Response Modifier"Dept. of Dermatology Yale Univ. School of Medicine.

Grass et al. "Inactivation of Leukocytes in Platelet Concentrates by Photochemical Treatment with Psoralen Plus UVA" The American Society of Hematology. Blood, vol. 91, No. 6 pp. 2180–2188.

TREATMENT OF INFLAMMATORY DISORDERS OF THE BOWEL AND URINARY BLADDER

This application is a provisional of Ser. No. 60/052,101 filed Jul. 10, 1997.

BACKGROUND OF THE INVENTION

Extracorporeal photopheresis is a process where 8-Methoxypsoralen (8-MOP), a naturally occurring light-sensitive compound, is administered orally two hours prior to treatment; blood is then withdrawn from the patient, anti-coagulated, and the white blood cells are separated by centrifugation and collected as a leukocyte enriched fraction. These 8-MOP containing leukocytes are then irradiated with ultraviolet A light (UVA) which binds the 8-MOP to pyrimidine bases in DNA and to intra- and extra-cellular proteins. These treated leukocytes are returned to the patient, and the result is an immunomodulation which has been found to be of clinical benefit in a number of disease states [Edelson R L. Photopheresis: a clinically relevant immunobiologic response modifier. [Review] Ann NY AcadSci. 191; 636:154–64].

There are a number of diseases which are felt to primarily involve T-cells or are T-cell mediated. Diseases such as cutaneous T-cell lymphoma, organ allograft rejection after transplantation, progressive systemic sclerosis (PSS), inflammatory bowel disease (IBD), rheumatoid arthritis (RA) and juvenile onset diabetes mellitus (JODM) are thought to be T-cell mediated.

Cutaneous T-cell lymphoma (CTCL) is a malignant disease that is progressive. Therapeutic options are limited. Edelson et al. performed a multi-center trial [Edelson R, Berger C, Gasparro F. et al. Treatment of cutaneous T cell lymphoma by extracorporeal photochemotherapy: Preliminary results. N Engl J Med 1987;316:297–303] which showed that 24 of 29 (83%) of erythrodermic patients experienced a significant improvement in their disease. These positive responses were seen at a median time of 22.4 weeks after initiation of therapy. Of clinical significance, these patients were those whose diseases were resistant to prior therapy which is felt to be a poor prognostic group. In addition, a decrease in the amount of peripheral blood involvement (Sezary cells) was seen. Actuarial data had indicated that median survival was increased to greater than 60 months from the onset of treatment in comparison with a historical median survival time of less than 30 months. In this original group of patients, remissions were sustained in eight of the subjects who were leukemic. Adverse reactions associated with photopheresis were rare.

Autoimmune diseases are characterized by a dysregulation of the immune system, characterized by specific cellular or humoral mediated destruction of specific organs or tissues in the patient. Examples of such diseases are rheumatoid arthritis and progressive systemic sclerosis.

Rheumatoid arthritis (R.A.) is an inflammatory disease that ultimately leads to joint destruction and is a generalized disease involving many organ systems. There are many pharmaceutical agents in use for R.A., however well tolerated agents with disease modifying potential are needed in as much as the disease is lifelong. In particular, a loss of efficacy and disease progression is seen in a high number of patients after starting secondary line therapy for R.A. Many of the second line agents are immunosuppressive and are themselves the reason for the major side effects such as infection. The need for development of a more specific, non-toxic immunomodulating therapy [Malawista S, Trock D, Edelson R. Treatment of rheumatoid arthritis by extracorporeal photochemotherapy: a pilot study. Arthritis Rheum 1991;34:646–54] is great.

Progressive systemic sclerosis (PSS) is a connective tissue disease characterized by inflammatory and fibrotic changes in the skin and viscera. Treatment has been difficult. Anti-inflammatory drugs and corticosteroids are helpful in the early stages of the disease, but do not appear to influence the progression of the disease. Trials with D-penicillamine, methotrexate, cyclosporine, calcium channel blockers and prostagladins are underway, but these agents do not appear to influence the overall progression of the disease. As this disease has been considered to be T-cell mediated, Rock and colleagues have treated PSS patients with photopheresis [Rook A H, Freundlich B, Jegasothy B V, et al. Treatment of systemic sclerosis with extracorporeal photochemotherapy: Results of a multicenter trial. Arch Dermatol 1992;128:337–46]. In this trial, 56 patients were enrolled into a randomized non-blinded clinical trial. A significantly higher response rate was seen in the photopheresis treated group (68% response rate) compared to the D-penicillamine (control) group (32% response rate).

Juvenile onset diabetes mellitus (JODM) is felt to be mediated by the immune system resulting in the destruction of the cells in the pancreas responsible for the production of insulin. Patients with this disorder have not only dysregulation of their blood sugar levels, but the disease is characterized by a vasculopathy, resulting in specific organ damage leading to significant morbidity and mortality.

IBD is either limited to the colon (ulcerative colitis) or affects both the colon and the small intestine. In addition, there are intraintestinal manifestations of the disease including pyoderma gangrenosum, erythema nodosum, sclerosing cholangitis, ankylosing spondylitis, hepatitis, arthritis, and uveitis. IBD involves a dysfunction of the immunoregulatory mechanisms that downregulate immune responses to digestion products, while maintaining the ability to develop a specific immune response to pathogens. Exposure to methoxsalen, activated by UV light, modulates immunoregulatory function, allowing the mucosal T-cells to mount a lower proliferative response to common microbial antigens than peripheral T-cells.

Other T-cell mediated phenomena include rejection of tissues that are foreign to the host. In the case of organ allograft transplantation, it is desirable to prevent rejection with respect to the transplanted organ, however to otherwise maintain the competence of the immune system, in order to allow the body to combat infection and to allow other normal body defenses. The standard treatments after transplantation are limited as the immunosuppression regimens are used to cause a state of generalized immunosuppression, which leads to microbial or opportunistic infection, the most common adverse reaction to this treatment. Immunomodulation which does not have broad immunosuppressive properties would be more desirable. Photopheresis has been shown to be effective, and investigators at Loyola University have been able to successfully treat with photopheresis 13 of 14 cases of cardiac rejection refractory to standard immunosuppressive agents. In a variation of this situation, photopheresis has been successfully used to treat a patient with chronic graft versus host disease [Rossetti et al., 1995, Transplant, 59:1, pp.149–151]. This disorder is characterized by an introgenically induced immunoincompetent host, where immune competent cells (bone marrow or peripheral stem cells) are infused into a patient in such situations as treatment for various malignancies and leukemia. Here the transplanted immunocompetent cells attack the patient (the "host"), and the issue is to modulate the immunocompetent cells without causing further broad immunosuppression and the side effects thereof Photopheresis involves the extracorporeal exposure of peripheral blood leukocytes to 8-methoxypsoralen (8-MOP) photoactivated by ultraviolet A light, followed by the reinfusion of the treated white blood cells.

8-methoxypsoralen molecules in the blood enter the white blood cell nuclei and intercalate in the double-strand DNA helix. In an extracorporeal circuit, long wave ultraviolet light is directed at the leukocyte-enriched blood fraction within the UVAR® Photopheresis System. The photoactivated drug, responding to the UVA energy, links to the thymidine base in the DNA helix. This results in cross-linking of thymidine bases which prevents the unwinding of the DNA during transcription. The plasma and altered leukocytes are then reinfused into the patient. The reinfusion of the photopheresis damaged leukocytes results in an delayed immune attack against these damaged leukocytes, as well as, otherwise unmodified WBC's displaying the same cell surface antigens.

Methoxsalen is a naturally occurring photoactive substance found in the seed of the Ammi majus (umbelliferae plant). It belongs to a class of compounds known as psoralens or furocoumarins. The chemical name is 9-methoxy-7H-furo[3,2-g][1]-benzopyran-7-one. The formulation of the drug is a sterile liquid at a concentration of 20 mcg/mL in a 10 mL vial. The pharmacokinetic activity of methoxsalen is available in the investigator's brochure [Investigator's Brochure for A Comparison Study of the Use of Extracorporeal Chemotherapy (ECP) With and Without Alpha Interferon in Treatment of Patients with Chronic HCV. June, 1996]. Toxicology studies of extracorporeal photochemotherapy and different dosages of UVADEX® and ultraviolet light in beagle dogs is located in the investigator's brochure.

UVAR System

The treatment consists of three phases including: 1) the collection of a buffy-coat fraction (leukocyte-enriched), 2) irradiation of the collected buffy coat fraction, and 3) reinfusion of the treated white blood cells. The collection phase has six cycles of blood withdrawal, centrifugation, and reinfusion steps. During each cycle, whole blood is centrifuged and separated in a pediatric pheresis bowl. From this separation, plasma (volume in each cycle is determined by the UVAR® Instrument operator) and 40 ml buffy coat are saved in each collection cycle. The red cells and all additional plasma are reinfused to the patient before beginning the next collection cycle. Finally, a total of 240 ml of buffy coat and 300 ml of plasma are separated and saved for UVA irradiation.

The irradiation of the leukocyte-enriched blood within the irradiation circuit begins during the buffy coat collection of the first collection cycle. The collected plasma and buffy coat are mixed with 200 ml of heparinized normal saline and 200 mcg of UVADEX® (water soluble 8-methoxypsoralen). This mixture flows in a 1.4 mm thick layer through the PHOTOCEPTOR® Photoactivation Chamber, which is inserted between two banks of UVA lamps of the PHOTOSETTE®. PHOTOSETTE® UVA lamps irradiate both sides of this UVA-transparent PHOTOCEPTOR® chamber, permitting a 180-minute exposure to ultraviolet A light, yielding an average exposure per lymphocyte of 1–2 $J/cm^2$. The final buffy coat preparation contains an estimated 20% to 25% of the total peripheral blood mononuclear cell component and has a hematocrit from 2.5% to 7%. Following the photoactivation period, the volume is reinfused to the patient over a 30 to 45 minute period.

Systems employing these techniques are known whereby extracorporeal treatment of a patient's blood is undertaken. For example, in U.S. Pat. No. 4,573,960—Goss, a patient is given a drug that requires photoactivation and the patient's blood is then withdrawn and separated into its components. The untreated components (red blood cells, some plasma, etc.) are returned to the patient. The patient is then disconnected from the treatment apparatus and the separated components, e.g., white blood cells, are exposed to ultraviolet light. Following photoactivation, the treated cells are returned to the patient.

In U.S. Pat. Nos. 4,321,919; 4,398,906; and 4,464,166, issued to Edelson, the external treatment methods for diseases in which there is a pathological increase of lymphocytes, such as cutaneous T-cell lymphoma, have been discussed. In these methods the patient's blood in the presence of a chemical or an antibody is irradiated with ultraviolet light. Ultraviolet light effects a bonding between the lymphocytes and the chemical or antibody thus inhibiting the metabolic processes of the lymphocytes.

A variety of human viruses are able to infect and replicate within mononuclear cells, or infectious viral particles may remain present within the mononuclear cells. The mononuclear cells can act as either a source for viral replication and spread of the virus, or as a reservoir of infectious virus particles which is difficult for the immune system to eliminate. Failure to eliminate these sources of infectious virus may lead to the establishment of a chronic condition. Viruses which can infect, replicate within, or reside in mononuclear cells include, but are not limited to, arthropod borne viruses, enteroviruses, paramyxoviruses (RSV), herpes viruses, cytomegalo-virus (CMV), Epstein-Barr virus (EBV), hepatitis B virus (HBV), hepatitis C virus (HCV), hepatitis D virus (HDV), hepatitis G virus (HGV), and retroviruses (such as HIV).

A variety of human non-viral pathogenic agents are able to infect and replicate within mononuclear cells, or the infectious non-viral pathogenic agents may remain present within the mononuclear cells. The mononuclear cells can act as either a source for replication and spread of the non-viral pathogenic agents, or as a reservoir of infectious non-viral pathogenic agents which is difficult for the immune system to eliminate. Failure to eliminate these sources of infectious non-viral pathogenic agents may lead to the establishment of a chronic condition. Non-viral pathogenic agents which can infect, replicate within, or reside in mononuclear cells include, but are not limited to, bacteria such as arthropod-borne bacteria, mycoplasma species, and mycobacteria species, and parasites such as plasmodium species and other arthropod-borne parasites.

Extracorporeal photopheresis (ECP) has been successfully used to treat HIV infection (U.S. Pat. No. 4,960,408) and psoralen compounds with long wavelength ultraviolet light have been shown to inactivate certain viruses in vitro, such as HIV (Quinnan, G.V. et al., 1986, Transfusion, 26, pp 481; Bisaccia, A. et al., 1990, Am. Intern. Med., 113, pp 270; Bisaccia, A. et al., 1991, Ann. NY Acad. Sci., 636, pp 321), and influenza virus and herpes simplex virus (Redfield, D. C. et al., 1981; Infect. and Immun., 32, pp 1216). Bisaccia has studied ECP in a pilot trial as therapy for patients with AIDS-related complex. The rationale was that a combination of psoralen with WVA activation could damage HIV in vitro and that reinfusion of the damaged virus may initiate an immune response. The authors found that ECP produced an increase in the HIV-Ab production, increase in the CD8(+) lymphocytes, a decrease in the p24 antigen titer and the inability to culture HIV in 3 patients. Eleven of the 20 patients had improvement in their skin test antigen reactivities.

In addition, a reduced incidence of infection episodes was reported in patients receiving photopheresis treatment for immunosuppression following transplant surgery (Meiser, B. M. et al., 1994, Transplantation, 57, pp. 563). However, the results observed for the transplant surgery patients did not correlate with photopheresis treatment since infection episodes in general were recorded including patients who received a variety of treatments to prevent rejection of the transplanted organ.

SUMMARY OF THE INVENTION

The present invention is drawn to a method of treating inflammatory bowel disorders, including including but not limited to IBD, Crohn's Disease, and ulcerative colitis, using extracorporeal photopheresis. In addition, the present invention is drawn to the treatment of inflammatory diseases of the urinary bladder, including but not limited to cystitis, such as interstitial cystitis. In particular, patients with IBD, Crohn's Disease, ulcerative colitis or interstitial cystitis are treated by the method of the present invention. The present invention is also drawn to the alteration or modulation of monocyte function in patients having inflammatory bowel disorders or inflammation of the urinary bladder through the use of the method of photopheresis. The method of treatment in the present invention involves the treatment of a patient's blood with a photoactivatable or photosensitive compound which is capable of binding to nucleic acids in infected nucleated cells upon activation of the compound by ultraviolet light. The photoactivatable or photosensitive compound may be administered to the patient's blood in vitro or in vivo by conventional administration techniques.

A portion of the patient's blood is then treated extracorporeally using photopheresis, which comprises subjecting the blood to ultraviolet light, preferably long wavelength ultraviolet light in the wavelength range of 320 nm to 400 nm, commonly called WVA light. The treated blood, or a fraction thereof, is returned to the patient following extracorporial photopheresis to modulate monocyte function and/ or stimulate an immunological response by the patient's immune system. The cellular genetic material is damaged by this treatment which may result in the alteration or modulation of monocyte function as disclosed herein.

DETAILED DESCRIPTION OF THE INVENTION

The present invention is directed to the use of photopheresis to treat patients having an inflammatory bowel disorder, including but not limited to IBD, Crohn's Disease, Ulcerative colitis or patients having an inflammatory disorder of the urinary bladder, including but not limited to cystitis, such as interstitial cystitis. While it is not intended that the scope of the present invention be limited by any specific theory of operation, it is believed that inflammatory bowel disorders and inflammatory disorders of the urinary bladder of a patient can be treated by using a photopheresis treatment according to the present invention.

Extracorporeal photochemotherapy using methoxsalen (photopheresis) is believed to cause an immunization against the abnormal (cancerous, in the case of CTCL) T-cells. During photopheresis, methoxsalen enters the white blood cell nuclei and intercalates in the double-strand DNA helix. In an extracorporeal circuit, long wave ultraviolet light is directed at the leukocyte-enriched blood volume. The methoxsalen, responding to the UVA energy, links to the thymidine base in the DNA helix. This results in the cross-linking of thyridine bases which prevent the unwinding of the DNA during transcription. Ultraviolet A light (UVA) damages abnormal T-cells rendering them more immunogenic. After cells are photoactivated, reinfusion of these altered T-cells causes an immunological reaction that targets T-cells carrying the same surface antigens[Edelson R L. Photopheresis: a clinically relevant immunobiologic response modifier. [Review] Ann NY Acad Sci. 191;636:154–64]. This results in the production of a highly specific immune response against the abnormal cells (either a cancer clone or perhaps T-cells which express viral antigens on their surface). It is estimated that approximately 25–50% of the total peripheral blood mononuclear cell 5 compartment is treated per photopheresis session (2 consecutive days schedule).

Work by Vowels [Vowels B R, Cassin M, Boufal M H, et al. Extracorporeal photochemotherapy induces the production of tumor necrosis factor-alpha by monocytes: Implications for the treatment of cutaneous T cell lymphoma and systemic sclerosis. J Invest Dermatol 1992;98:686–92]. demonstrated monocytes treated in an extracorporeal circuit of plasma containing 8-methoxypsoralen and exposure to ultraviolet-A light (photopheresis) releases tumor necrosis factor-alpha, IL-1, IL-6, and possibly IL-8. It is believed that photopheresis modulates the activity of peripheral blood monocytes/macrophages.

According to the claimed methods, a photoactivatable or photosensitive compound is first administered to the blood of a patient who has an inflammatory bowel disorder or an inflammatory disorder of the urinary bladder. The photoactivatable or photosensitive compound may be administered in vivo (e.g. orally or intravenously) or may be administered in vitro to a portion of the patient's blood which has been removed from the patient by employing conventional blood withdrawal techniques.

In accordance with the present invention, the photoactivatable or photosensitive compound should be capable of binding to nucleic acids upon activation by exposure to electromagnetic radiation of a prescribed spectrum, e.g., ultraviolet light.

Next, the portion of the patient's blood to which the photoactive compound has been administered is treated by subjecting the portion of the blood to photopheresis using ultraviolet light. The photopheresis step is preferably carried out in vitro using an extracorporeal photopheresis apparatus. The photopheresis step in accordance with the present invention may also be carried out in vivo. A presently preferred extracorporeal photopheresis apparatus for use in the methods according to the invention is currently manufactured by Therakos, Inc., under the name UVAR®. A description of such an apparatus may be found in U.S. Pat. No. 4,683,889. The exposure of blood to ultraviolet light in a photopheresis apparatus is within the ability of persons having ordinary skill in the art.

When the photopheresis step is carried out in vitro, at least a fraction of the treated blood is returned to the patient. Preferably, the treatment method described herein is repeated at an interval of about once per week to about once every four weeks. Preferred photoactive compounds for use in accordance with the present invention are compounds known as psoralens (or furocoumarins) as well as psoralen derivatives such as those described in U.S. Pat. No. 4,321, 919 and U.S. Pat. No. 5,399,719. Alternatively, the patient's blood can be separated on a standard apheresis-type device and photoactivated on a separate device.

The preferred photoactivatable or photosensitive compounds for use in accordance with the present invention include, but are not limited to, the following: Psoralen and psoralen derivitaves; 8-methoxypsoralen; 4,5'8-trimethylpsoralen; 5-methoxypsoralen; 4-methylpsoralen; 4,4-dimethylpsoralen; 4-5'-dimethylpsoralen; 4'-aminomethyl-4,5',8-trimethylpsoralen; 4'-hydroxymethyl-4,5',8-trimethylpsoralen; 4',8-methoxypsoralen; and a 4'-(omega-amino-2-oxa) alkyl-4,5', 8-trimethylpsoralen, including but not limited to 4'-(4-amino-2-oxa)butyl-4,5',8-trimethylpsoralen. The most particularly preferred photosensitive compound for use in accordance with the invention is 8-methoxypsoralen.

The photosensitive compound, when administered to the patient's blood in vivo is preferably administered orally, but also can be administered intravenously and/or by other conventional administration routes. The preferred oral dosage of the photosensitive compound is in the range of about 0.3 to about 0.7 mg/kg. most preferably about 0.6 mg/kg.

When administered orally, the photosensitive compound should preferably be administered at least about one hour prior to the photopheresis treatment and no more than about three hours prior to the photopheresis treatment. If administered intravenously, the times would be shorter.

Alternatively the photosensitive compound may be administered to the patient's blood following its withdrawal from the patient, and prior to or contemporaneously with exposure to ultraviolet light. The photosensitive compound may be administered to whole blood or a fraction thereof provided that the target blood cells or blood components receive the photosensitive compound.

The photopheresis treatment in the treatment methods according to the present invention is preferably carried out using long wavelength ultraviolet light (UVA) at a wavelength within the range of 320 to 400 nm. The exposure to ultraviolet light during the photopheresis treatment preferably has a duration of sufficient length to deliver about 1–2 J/cm$^2$ to the blood.

When the photopheresis treatment according to the present invention is carried out in vivo, careful attention should be paid to controlling the maximum radiant exposure so as to avoid unnecessary injury to the patient. Methods for calculating maximum radiant exposure to ultraviolet light are known in the art.

First, a photosensitive compound as described hereinabove is administered to at least a portion of the donor's blood either prior to removal of the blood, either orally or intravenously, or after removal from the patient in which case it is administered in vitro. Optionally, a portion of the donor's blood could first be processed using known methods to substantially remove the erythrocytes and the photoactive compound is then administered to the resulting enriched leukocyte fraction.

In any case, the portion of blood (or enriched leukocyte fraction thereof) to which the photosensitive compound has been administered is subjected to a photoactivation treatment using ultraviolet light, preferably UVA in the manner previously described. The treated blood or the treated enriched leukocyte fraction (as the case may be) is then administered back to the donor.

Current treatment for inflammatory bowel disorders include chemotherapeutic agents such as aminosalicylates, corticosteroids, and immunosuppressants. Significant side effects from these chemotherapeutic treatments occur. Many patients develop side effects from aminosalicylates before achieving a therapeutic dose. The side effects of nausea, malaise, headache, and myalgia often result in patient non-compliance. The side effects of long term corticosteroids use (Cushingoid appearance, hypertension, cataract formation, osteoporosis and aseptic necrosis) are well documented. In addition, although corticosteroids may be effective in treating a flare in disease, the ability of these drugs to prevent relapse has never been proven. An increased risk of developing cancer, neutropenia and bone marrow suppression is well documented in the organ transplant recipient population.

A summary description of certain inflammatory bowel disorders which are treated in the method of the present invention, include but are not limited to:

1. Ulcerative Colitis

Ulcerative colitis is a mucosal disorder which affects the colon and is associated with significant morbidity and mortality. There are associated extraintestinal manifestations of this disease which include arthritis, ankylosing spondylitis, hepatitis, uveitis, pyoderma gangrenosum, erythema nodosum, and sclerosing cholangitis. Cancer can occur in areas of chronic inflammation. Specific symptoms of ulcerative colitis include diarrhea, bowel bleeding, weight loss, and abdominal pain and cramping. This disease can affect individuals of any age. Children with this disease fail to grow and develop normally.

2. Crohn's Disease

Crohn's disease is characterized by focal, transmural and asymmetric inflammation involving one or more segments of the alimentary canal extending anywhere from the mouth to the anus. The most commonly involved areas include the distal ileum and right colon. Exclusive colonic involvement occurs in about 20% and disease limited to the small bowel occurs in 15–20% in patients affected with Crohn's disease. The ulcerations associate with Crohn's disease extend linearly, often isolating pockets of normal mucosa, giving this disease a characteristic cobblestone appearance.

A summary description of certain inflammatory disorders of the urinary bladder which are treated in the method of the present invention, include but are not limited to:

1. Interstitial Cystitis (IC)

Interstitial cystitis (IC) is a chronic severe bladder disorder similar to IBD in that it is an autoimmune disease that manifests itself as an attack on the bladder wall rather than the bowel wall. Like IBD, IC histologically can be identified as a unifocal or multifocal inflammatory infiltration of the bladder wall with mucosal ulceration and scarring. It results in contraction of the smooth muscle, diminished urinary capacity, symptoms of frequency, hematurea, urgency, nocturia, painful urination and suprapubic pelvic pain.

Treatments such as amitriptyline, hydroxyzine, dimethyl sulfoxide, chlorpactin and heparin may improve symptoms but do not alter the long term course of the disease.

The result of the treatment method of the present invention for inflammatory bowel disorders, including but not limited to IBD, Crohn's Disease and for inflammatory disorders of the urinary bladder including but not limited to cystitis, such as IC, is an elimination of the symptoms of the disease, reflected as a reduction in the activity index for the disease and/or a significant reduction in steroid dose (particularly for those who are steroid dependent) and/or the avoidance of surgery (removal of the affected tissue) and increasing symptom-free intervals in these patients.

The following Examples are provided to illustrate the present invention and are not to be construed as a limitation thereon.

EXAMPLE 1

EXTRACORPOREAL PHOTOCHEMOTHERAPY IN THE TREATMENT OF PATIENTS WITH ULCERATIVE COLITIS

I. Description of the Patient Population

Patients who have an acute flair of their ulcerative colitis were the subjects of this clinical investigation. To be included for inclusion into this protocol, the following inclusion/exclusion criteria had to be met:

Patients must be 40 kg

Females of childbearing potential must be urine pregnancy test negative within 24 hours prior to starting the study treatment. Effective birth control must be practiced from one month prior to the study treatment to the end of treatment phase of the protocol. Females may not be lactating.

Pre-study laboratory values of:
  WBC greater than 3.0 cmm
  Hemoglobin greater than 6.5 mg/dL
  Platelet count >75,000/UL
  Prothrombin time not more than 3 seconds beyond the normal range Able to provide informed consent Adequate venous access Able and willing to comply with the study protocol and medication schedules The diagnosis of ulcerative colitis must be confirmed by the history and physical exam, endoscopic and histologic evaluation. The extent of disease must be at least 10 cm from the anal verge.

To qualify for the study:
  The patient must be experiencing an acute, moderate to severe relapse of their UC and will meet at least three of the seven criteria listed:
    Diarrhea >6/day
    Gross blood in the stool
    Fever >37.7
    Heart rate >90/min
    Anemia less than 75% of the normal
    ESR >30
    Steroid dependent
      or
    Candidate for surgical intervention II. Description of the Treatment Freguency and Efficacy Parameters Photopheresis treatments were performed on two consecutive days for four weeks (8 photopheresis treatments) and then were performed on two consecutive days every other week for the next eight weeks (8 additional treatments) for a total of 16 photopheresis procedures over 12 weeks. (Defined as treatment period I). The goal of treatment period I was to assess the primary efficacy parameters (disease activity index [DAI], assess need for surgical intervention, assess ability of patients to wean from steroids or other immunosuppressive medications used to control UC symptoms and to assess the response to treatment on an endoscopicallhistological level). For the purpose of this protocol, a successful response to treatment was defined as:

A 50% decrease in the disease activity index (DAI), the avoidance of surgery or the reduction/elimination of steroids and improvement in endoscopy grade and histology are all considered to be clinically significant.

After treatment phase I was completed, the patient was then followed for nine months upon the discontinuation of treatment. Flares (as evidenced by increase in ulcerative colitis symptomatology [diarrhea, bleeding and pain]) during this follow-up period were treated with photopheresis, at the Investigator's discretion. The goal of this follow-up protocol was to calculate: (1) disease free intervals, (2) to determine whether flares in disease can be controlled by photopheresis, and (3) to provide data on weaning from photopheresis therapy.

III. Description of the Efficacy Assessments:

During the treatment and follow-up periods, the patient had the following efficacy assessments:

A. Disease activity index: This is a modified Truelove and Witts scale as described by Lichtiger, et.al. (Table 1). This scale assesses the number of bloody bowel movements, presence of nocturnal diarrhea, incontinence, abdominal pain, general well-being, and abdominal tenderness. The minimum score is 0. The maximum score is 21. Scores of 12 or higher are considered to be in the severe category. Significant improvement indicates a decrease in DAI by 50%. Scores less than 4 indicate clinical remission.

TABLE 1

Disease Activity Index

| Disease Activity | Score |
|---|---|
| Diarrhea (number of daily stools) | |
| 0–2 | 0 |
| 3–4 | 1 |
| 5–6 | 2 |
| 7–9 | 3 |
| >10 | 4 |
| Nocturnal diarrhea | |
| No | 0 |
| Yes | 1 |
| Visible blood in stool (% of BM) | |
| 0% | 0 |
| <50% | 1 |
| >50% | 2 |
| 100% | 3 |
| Fecal incontinence | |
| No | 0 |
| Yes | 1 |
| Abdominal pain | |
| None | 0 |
| Mild | 1 |
| Moderate | 2 |
| Severe | 3 |
| General well-being | |
| Perfect | 0 |
| Very Good | 1 |
| Good | 2 |
| Average | 3 |
| Poor | 4 |
| Terrible | 5 |
| Abdominal tenderness | |
| None | 0 |
| Mild and Iocalized | 1 |
| Mild to moderate and diffuse | 2 |
| Severe or rebound | 3 |
| Need for anti-diarrheals | |
| No | 0 |
| Yes | 1 |

B. Endosconic findings were scored according to a modified scale determined by Blackstone, et.al., which assesses severity of mucosal granularity, vascular pattern, friability, ulceration, and mucopus. Analysis of endoscopic findings were analyzed separately from the symptom assessment scores (Table 2). Included in the endoscopic assessment were determination of the length of endoscopic disease and its corresponding mucosal severity.

TABLE 2

Endoscopic Mucosal Severity Score

| Activity | Score | Appearance |
|---|---|---|
| Quiescent | 0 | Distorted or absent mucosal vascular pattern<br>Granularity |
| Mild | 1 | Continuous or focal erythenia<br>Friability |
| Moderate | 2 | Mucopurulent exudate<br>Single or multiple ulcers (<5 mm), fewer than 10/10 cm segment |
| Severe | 3 | Large ulcers (>5 mm), more than 10 per 10 cm segment<br>Spontaneous bleeding |

C. Histology: were scored by one Pathologist. The histology grading score is a system which grades both activity and severity of disease. Histology index (or score) were expressed by adding the values for all five criteria and this total was expressed as the total out of a maximum total score of fifteen.

1. ACTIVITY INDEX
   Criterion #1: NEUTROPHIL LEUKOCYTES IN INTACT LAMINA PROPRIA
      Method: The number of neutrophils in one high power (x40) field of the most actively inflamed area of intact mucosa were counted. Ulcer debris and granulation tissue were excluded.
         0=no neutrophils
         1=1–10/hpf
         2=11–20/hpf
         3=>21l/hpf
   Criterion #2 ACUTE CRYPTITIS
      Method: Evaluate neutrophil infiltration of crypts, including crypt abscesses and crypt destruction by the acute inflammation.
         0=no cryptitis
         1=crypt infiltration by neutrophils; no crypt abscesses; no active crypt destruction
         2=crypt abscesses +; no active crypt destruction
         3=active crypt destruction
   Criterion #3 EROSION/ULCERATION
         0=no erosion or ulceration
         1=focal partial thickness mucosal erosion only
         2=presence of acutely inflamed necrotic tissue devoid of mucosa (=superficial ulcer)
         3=presence of acutely inflamed granulation tissue (=deep ulcer)

2. DISEASE CHRONICITY INDEX
   Criterion #4 CRYPT ARCHITECTURE
         0=normal
         1=mild distortion
         2=moderate distortion with definite branching
         3=severe distortion
   Criterion #5 CHRONIC INFLAMMATION IN LAMINA PROPRIA
      Method: Assess lymphocyte, plasma cell and eosinophil numbers (subjective, no count)
         0=normal
         1=mild increase
         2=moderate increase
         3=severe disease Adverse events were assessed as follows:
   The frequency and severity of adverse events classified by their relationship to the device, drug and disease
   The frequency of abnormal laboratory parameters and new symptomatology at each treatment visit.

IV. Sample Schedule of Assessments
   A. Baseline Assessments (within 48 hours of the first photopheresis treatment)
      CBC
      Chemistry
      Sedimentation rate
      Disease activity index (DAI)
      Concomitant medication listing
      Endoscopy with histological evaluation
      Quality of life questionnaire
   B. Prior to each two day photopheresis session
      CBC
      Concomitant medication listing
   C. Every two weeks during the treatment phase
      Chemistry panel
      Sedimentation rate
      Disease activity index (DAI)
   D. Pre-tx #5
      Quality of life questionnaire
   E. Monthly
      Urine pregnancy test (if applicable)
   F. At Weeks 6 and 12 of photopheresis treatment
      Endoscopic and histological evaluation
      Quality of life questionnaire
      CD4/CD8 (week #12 only)
   G. Post Treatment Evaluation
      One Month Following Last Treatment in Period I
      CBC
      Sedimentation rate
      Chemistry
      Disease activity index (DAI)
      CD4/CD8
      Quality of life questionnaire
      Concomitant medication listing
      Months 3, 6 and 9
      CBC
      Sedimentation rate
      Chemistry
      Disease activity index (DAI)
      Quality of life questionnaire
      Concomitant medication listing
      Months 2, 4, 5, 7 and 8
      Disease activity index (DAI)

V. Results
Patient #1/1

| Assessment | Screening Visit | Pre-Photo Tx #5 | Pre-Photo Tx #9 | Pre-Photo Tx #11 | Pre-Photo T #13 | Pre-Photo Tx #15 |
|---|---|---|---|---|---|---|
| UC Histology Activity Score | 6 | | 1 | | | |
| UC Chronicity Score | 3 | | 2 | | | |
| Endoscopy Score | 2 | | 1 | | | |
| Cm UC involvement from anal verge | 20 | | 10 | | | |
| Quality of Life Questoinnaire | 151 | 169 | | 208.5 | | |
| ESR | 9 | 7 | 7 | | 9 | |
| Disease Activity Index | 8 | 5 | | 2 | 2 | |
| | 2/20/98 | 3/12/98 | | 4/17/98 | 5/2/98 | |

Summary: 26 year old female with endoscopically and histologically confirmed diagnosis of ulcerative colitis.

Baseline Evaluation: Entered the protocol having diarrhea greater than 7–9 times per day, fecal incontinence, gross blood in the stool and a fever greater than 37.7. Colonoscopy showed mucosal changes from 20 to 0 cm. The findings included an erythematous appearance, superficial erosions, aphthoid erosions and areas of frank hemorrhage. The histology activity score was 6, the UC chronicity score was 3 and the endoscopy score was 2. The patient's disease activity index was 8 of 20 and the patient's quality of life questionnaire totaled 151 of a possible 224 points. Patient reported on the patient diary to feel "fair" and be experiencing "moderate" pain.

Two Week Evaluation: The patient's disease activity index fell to 5 of 20, with the major areas of improvement being noted as a decreased number of episodes of diarrhea to 3–4 times per day and no fecal incontinence. The patient's quality of life increased to 169 out of a possible 224 points. The patient reported on the patient diary to feel "well" with only "mild" pain, the patient still reported blood in the stool.

Six Week Evaluation: The patient's disease activity index fell to 2 of 20, with the major area of improvement being noted as a decreased number of episodes of diarrhea to 0–2 times per day and no fecal incontinence. The patient's quality of life increased to 208 out of a possible 224 points. The patient reported on the patient diary to feel "very well" with "no" pain and reported many more days without blood in the stool. Sigmoidoscopy showed mucosal changes in the rectum, with both erythematous and granular changes. The visualized colon (up to 30 cm) were grossly normal. The UC histology score decreased from 6 to 1, UC chronicity score decreased from 3 to 2 and the endoscopy score reduced from 2 to 1.

| Assessment | Screening Visit | Pre-Photo Tx #1 | Pre-Photo Tx #3 | Pre-Photo Tx #5 |
|---|---|---|---|---|
| UC Histology Activity Score | 4 | | | |
| UC Chronicity Score | 0 | | | |
| Endoscopy Score | 2 | | | |
| Cm UC involvement from anal verge | 40 | | | |
| Cm UC involvement from anal verge | 40 | | | |
| Quality of Life Questionnaire | Total score = 188 | | | Total score = 212 |
| ESR | | 15 | | |
| Disease Activity Index | 3 | 3 | | 3 |
| | | | | 4/23/98 |
| | X | | | |
| | X | | | X |
| Concomitant Med Listing | Prednisone 20 mg QOD | Pred 20 mg QOD | Pred 15 mg QOD | Pred 10 mg QOD |

Patient UC 1/3

Summary: 42 year old male with a 5+year history of steroid dependency to control ulcerative colitis symptoms.

Baseline Evaluation: Entered the protocol with bloody stools, colonoscopy showing mucosal changes from 0 cm to 40 cm. Endoscopy findings included edema, an erythythematous and friable appearance, aphthoid erosions, (a rim of erythema, a yellow-gray central crater, absence of a raised margin), a blurred/blunted vascular pattern. DAI was 3 and patient was receiving Prednisone 20 mg every other day. Baseline quality of life was 188 out of a possible 224 points.

Two Week Evaluation: DAI still 3, but patient has been weaned down to Prednisone 10 mg every other day, with no increase in symptoms. Quality of life has increased from 188 to 212.

EXAMPLE 2

EXTRACORPOREAL PHOTOCHEMOTHERAPY IN THE TREATMENT OF PATIENTS WITH CROHN'S DISEASE

I. Description of the Patient Population

Patients who have an acute flair of their Crohn's disease are the subjects of this clinical investigation. To be included for inclusion into this protocol, the following inclusion/exclusion criteria were met:

A. Inclusion Criteria

Age between 18 and 65

Diagnosis of Crohn's disease according to Malchow's criteria and Crohn's activity index (CDAI)

Radiological and/or endoscopic and/or sonographic localization documented within the last 12 months before the start of the study Steroid dependent disease course with a documented treatment of at least 10 mg of prednisone per day for at least the last three months needed in order to achieve a remission (remission is defined as a CDAI <200 for two successive weeks). The steroid dependence must be confirmed by a history of at least one relapse (CDAI >200) in an attempt to reduce the steroid dose to <10 mg Written or oral consent in the presence of witness after the patient has been informed thoroughly by the treating physician Before beginning treatment, all women of childbearing age must give a documented negative serum beta-HCG pregnancy test within 24 hours before the first treatment. In addition, they must agree to follow an adequate form of contraception during the study No known allergy to heparin or to 8-methoxypsoralen B. Exclusion Criteria Patients unable to cooperate with the screening or treatment procedures Patients with a high likelihood of needing surgical intervention because of bleeding, abscess or peritonitis Patients with clinically relevant stenosis of the gastrointestinal tract Patients with intestinal stoma Concurrent or previous exposure within the last three months of treatment with cyclosporin-A No previous exposure (within the last three months) or a stable dose of azathioprine within the last three months More than three antibiotic treatment phases with ciproxin or metronidazole over a period of fourteen days each within the last three months with confirmed identification of the pathogen Nursing or pregnant women Patients with a serious concomitant illness Cardiovascular instability which would not allow the required volume of blood to be withdrawn during photopheresis Treatment with drugs with known photosensitizing potential Patients with poor venous access Patients with HIV, Hbs antigen or HCV positivity Patients with the following laboratory findings:
  hemoglobin less that 10.5 g/dL
  platelets less than $100 \times 10^9$/L
  WBC $<4000 \times 10^9$/1
  serum bilirubin >3 mg/dL
  serum creatinine >2 mg/dL
  PT <60%, PTT >50 sec II. Description of the Treatment Frecuency and Efficacy Parameters A. Treatment Frequency and Efficacy Assessments Preliminary Phase 0

In the preliminary phase of the study, the patients who meet the inclusion criteria or who could meet them in future observation were selected. Retrospective documentation of the steroid-dependent course of the patient's disease must be guaranteed.

Each patient's CDAI was determined six weeks before the start of the study. In the next six weeks, the patient was stabilized at the maintenance dose, which was the lowest dose of steroid that ensures inactivity of the Crohn's symptoms (defined as a CDAI <200 to two successive weeks). The patients were brought into the study at the maintenance dose which must be >10 mg of prednisone per day.

Further monitoring of the patients took place within the first week before the start of the study (week −1).

Assessment at Week (−1):

Demographics

History of Crohn's disease

Localization of Crohn's disease

Previous surgical history

Previous treatment for Crohn's disease

Documentation of evidence of steroid dependence according to the definition of the inclusion criteria History and physical Laboratory assessment (CBC with differential, ESR, CRP, $\alpha$1-acid glycoprotein, serum electrolytes, creatinine, BUN, SGOT, SGPT, bilirubin, $\gamma$-GT, serum glucose, PTT, PT and urinalysis Serum frozen for future study

CDAI

Documentation of extraintestinal manifestations of Crohn's disease

Concomitant medication listing

Urine $\beta$-HCG test (when applicable)

Compliance check

Triple permeability test: sucrose, lactulose, mannitol

Quality of life index

Preliminary Phase 1

Patients who met the inclusion criteria were introduced into the study during the six-month preliminary phase. Prospective documentation of the disease activity and the cumulative steroid dose in the preliminary phase must be guaranteed.

In the preliminary phase, continuous attempts to reduce steroid dose were made according to a fixed steroid reduction schedule. Repeated attempts were made to reduce the dose to a level lower than the maintenance dose according to the respective schedule. The maintenance dose is was reduced permanently in the actual treatment phase.

The patient's clinical activity, measured by CDAI, was used as the criterion for deciding on whether to wean steroids as per the steroid weaning schedule.

Steroid reduction began with the first day of treatment in phase 1. The dosage was reduced by alternating the initial steroid dose with the next lower dose level of a standard dosage series (i.e., 50 mg, 37.5 mg, 25 mg, 15 mg, 10 mg, 5 mg) for two weeks. For the next two weeks, an attempt was made to reduce the dose to this level. If the clinical remission is maintained (no increase in CDAI >60 above the initial level or >200 after the second week), the steroid dose is reduced by an additional dose level for four weeks, as described above.

A recurrence of the primary illness (increase in CDAI >60 over the starting value or >200 over two weeks) was treated by returning the steroid dose to the next higher dose level of the dosage series for two weeks previous to the flare. If clinical remission cannot be achieved with this dose (CDAI <200 for two weeks), the steroid dose is increased to 50 mg per day for one week with subsequent reduction of dose according to the standard steroid weaning schedule.

However, the dose was only reduced to the dose at which a clinical remission was most recently observed. This dose may be different from the maintenance dose and is referred to as the "remission stabilization dose," the dose is again reduced according to the steroid weaning schedule. The possibility cannot be ruled out that the maintenance dose at the end of the treatment phase differs from that of the preliminary phase of the study.

The clinical course of the patient's Crohn's disease was stable for the last two weeks before the start of the photopheresis treatment phase.

In the last two weeks before the start of the photopheresis treatment phase, the patient was given a Crohn's diary for documenting the symptoms associated with their disease.

In the preliminary phase, blood sample for CBC with differential, chemistry, CRP and α1-acid glycoprotein was obtained every four weeks.

Treatment Phase

Photopheresis treatments were performed on two consecutive days on a monthly basis for six months.

Prior to the first day of treatment at each one of the monthly visits, the following assessments were performed:

Assessment of clinical status

CDAI

Documentation of extraintestinal symptoms of Crohn's disease

Documentation of steroid dose and other concomitant medications

Laboratory assessment: blood samples for CBC with differential, chemistry, CRP and α1-acid glycoprotein Assessment of adverse events Quality of life index Permeability test (months 0 and 6 only)

Colonoscopy with biopsy is optional

Steroid reduction began with the first day of treatment. The dose reduction amounts to 5 mg of prednisone in four week according to the standard steroid weaning schedule. Relapses of Crohn's disease with CDAI values of more that 450 lead to termination of the study.

III. Results

The Effect of Photopheresis on 5 Crohn's Disease Patients (Arithmetic mean standard deviation, median and range)

EXAMPLE 3

EXTRACORPOREAL PHOTOCHEMOTHERAPY IN THE TREATMENT OF PATIENTS WITH INTERSTITIAL CYSTITIS

I. Description of the Patient Population

Patients who have an acute flair of their interstitial cystitis are the subjects of this clinical investigation. To be included for inclusion into this protocol, the following inclusion/exclusion criteria are to be met:

A. Inclusion Criteria

Age between 18 and 65

Written or oral consent in the presence of witness after the patient has been informed thoroughly by the treating physician Before beginning treatment, all women of childbearing age must give a documented negative serum beta-HCG pregnancy test within 24 hours before the first treatment. In addition, they must agree to follow an adequate form of contraception during the study No known allergy to heparin or the 8-methoxypsoralen Patient must have pain in bladder upon filling and relief upon emptying bladder and Patient must have suprapubic, pelvic, urethral, vaginal or perineal pain and Patient must have waking frequency of micturation >5 time per day and nocturia >2 times per night and Patient must have glomerulation after hydrodistention on cystoscopy

OR

Hunner's ulcer

B. Exclusion Criteria

Patients unable to cooperate with the screening or treatment procedures

Patients with benign or malignant bladder tumors

Patients with radiation, bacterial or cyclophosphamide induced cystitis

Patients with vaginitis

Patients with symptomatic urethral diverticulum

| | 24-Week Pre-Photopheresis Observation Period | | | 24-Week Photopheresis Treatment Period | | | Changes observed during the 24-week photopheresis treatment period minus the the changes observed during the 24-week prephotopheresis observation period |
|---|---|---|---|---|---|---|---|
| Parameter | Baseline | Final | Final Minus Baseline | Baseline | Final | Final Minus Baseline | |
| CDAI | 173.2 ± 72.5 MD = 167 (95 to 278) | 183.6 ± 65.4 MD = 181 (115 to 265) | 10.4 ± 90.7 MD = -5 (-97 to 137) | 166.2 ± 69.1 MD = 181 (53 to 230) | 132.8 ± 50.7 MD = 114 (86 to 191) | -33.4 ± 77.0 MD = -19 (-144 to 61) | -43.8 ± 157.9 MD = -62 (-281 to 103) |
| Prednisone Usage (Mg) | 78.0 ± 59.6 MD = 70 (25 to 175) | 101.0 ± 43.8 MD = 85 (70 to 175) | 23.0 ± 34.4 MD = 15 (-15 to 70) | 93.0 ± 40.2 MD = 90 (55 to 160) | 45.5 ± 45.8 MD = 35 (7.5 to 125) | -47.5 ± 14.1 MD = -55 (-62.5 to -30) | -70.5 ± 46.6 MD = 70 (-125 to -15) |
| Patient Weight (Kgs) | 67.4 ± 4.8 MD = 67 (62 to 74) | 67.8 ± 5.8 MD = 66 (64 to 78) | 0.4 ± 3.04 MD = 1 (-4 to 4) | 67.6 ± 5.9 MD = 65 (64 to 78) | 68.4 ± 7.4 MD = 66 (62 to 81) | 0.8 ± 2.4 MD = 2 (-3 to 3) | 0.4 ± 1.7 MD = 0 (-1 to 3) |

During this treatment phase, steroids were reduced and Crohn's disease symptoms were controlled (CDAI <200) while receiving photopheresis.

Patients with uterine, cervical, vaginal or urethral cancers

Patients with active herpes

Patients with bladder or lower urethral calculi

Symptoms of cystitis are relieved by antibiotics, urinary antiseptics, urinary analgesics Duration of symptoms has been less than 12 months Patient has involuntary bladder contractions by urodynamics At a bladder capacity of 400 mL, there is an absence of sensory urgency Nursing or pregnant women Patients with a serious concomitant illness Cardiovascular instability which would not allow the required volume of blood to be withdrawn during photopheresis Treatment with drugs with known photosensitizing potential Patients with poor venous access Patients with HIV, Hbs antigen or HCV positivity Patients with the following laboratory findings:
hemoglobin less than 10.5 g/dL
platelets less than $100 \times 10^9$/L
WBC $<4000 \times 10^9$/L
serum bilirubin >3 mg/dL
serum creatinine >2 mg/dL
PT<60%, PTT>50 sec II. Description of the Treatment Frecuency and Efficacy Photopheresis treatments are performed on two consecutive days weekly for four weeks (8 photopheresis treatments) and then are performed on two consecutive days every other week for the next eight weeks (8 additional treatments) for a total of 16 photopheresis procedures over 12 weeks. Photopheresis is weaned after 12 weeks to a frequency of monthly and beyond, depending on the patient's long-term response. The treatment can be reinitiated to treat a disease flare.

A significant reduction in pain, hematuria and frequency of urination is expected resulting from the treatment method of this invention. The type and amount of concomitant medications that the patients require for treatment of IC is reduced, resulting in an overall increase in the quality of life and disease reduction.

What is claimed is:

1. A method for treating an inflammatory bowel disorder in a patient, comprising:
   a) administering to said patient's blood a photoactivatable compound;
   b) treating at least a portion of said patient's blood of step a) with light in a wavelength that activates said photoactivatable compound; and
   c) returning at least a portion of said patient's blood of step b) to said patient.

2. The method of claim 1 wherein said inflammatory bowel disorder is selected from the group consisting of IBD, Crohn's Disease, and ulcerative colitis.

3. The method of claim 1 wherein said photoactivatable compound is a psoralen or psoralen derivative.

4. The method of claim 3 wherein said psoralen or psoralen derivative is 8-methoxypsoralen.

5. A method for treating an inflammatory disorder of the urinary bladder in a patient, comprising:
   a) administering to said patient's blood a photoactivatable compound;
   b) treating at least a portion of said patient's blood of step a) with light in a wavelength that activates said photoactivatable compound; and
   c) returning at least a portion of said patient's blood of step b) to said patient.

6. The method of claim 5 wherein said inflammatory disorder of the urinary bladder is cystitis.

7. The method of claim 5 wherein said inflammatory disorder of the urinary bladder is interstitial cystitis.

8. The method of claim 5 wherein said photoactivatable compound is a psoralen or psoralen derivative.

9. The method of claim 8 wherein said psoralen or psoralen derivative is 8-methoxypsoralen.

* * * * *